United States Patent [19]

Sawakata et al.

[11] 4,299,495
[45] Nov. 10, 1981

[54] DENSITY METER

[75] Inventors: Akira Sawakata, Fussashi; Hiroshi Yamamuro, Yokohamashi; Syouzou Kobayashi, Hachiojishi, all of Japan

[73] Assignee: Tokyo Shibaura Denki Kabushiki Kaisha, Kawasaki, Japan

[21] Appl. No.: 150,583

[22] Filed: May 16, 1980

[30] Foreign Application Priority Data

May 17, 1979 [JP] Japan .................. 54-60665

[51] Int. Cl.³ ............................. G01N 21/01
[52] U.S. Cl. .................... 356/442; 250/573
[58] Field of Search .............. 356/440–442; 250/573, 576

[56] References Cited

U.S. PATENT DOCUMENTS

| 3,319,514 | 5/1967 | McAllister et al. | 356/442 |
| 3,731,091 | 5/1973 | Rosso et al. | 250/573 X |
| 3,734,629 | 5/1973 | Griffiths et al. | 356/440 |
| 3,787,703 | 1/1974 | Topol | 250/576 X |

Primary Examiner—John K. Corbin
Assistant Examiner—Bruce Y. Arnold
Attorney, Agent, or Firm—Oblon, Fisher, Spivak, McClelland & Maier

[57] ABSTRACT

A density meter which is immersed in a liquid to be measured to optically measure the degree of opacity thereof is disclosed. The meter comprises a density measurement system in which the liquid is sucked into a transparent inner cylinder by moving a piston upwardly and the transmittance of the liquid is measured by an optical system provided outside the transparent inner cylinder, and a calibration system in which a calibration liquid flow path is formed. The outlet of the calibration liquid flow path is communicated with the transparent inner cylinder, and the outlet is above a position at which the end of the piston is set during density measurement. In calibration, the piston is raised to a position higher than the position of the outlet to introduce a calibration liquid into the inner cylinder to calibrate the density meter by the optical system.

5 Claims, 5 Drawing Figures

DENSITY METER

BACKGROUND OF THE INVENTION

1. Field of the Invention

This invention relates to a density meter which is inserted directly into a muddy liquid to measure the degree of opacity thereof, and more particularly to a density meter which is maintained in the muddy liquid for the calibration thereof.

2. Description of the Prior Art

In a measurement device utilizing optical means for measuring the density of a liquid, a muddly liquid is irradiated by a light emitting unit provided on one side of a container sampling the muddy liquid. Light passed through the muddy liquid and/or light scattered by suspended solids in the muddy liquid is received by a light receiving unit, and the output signal level of the light receiving unit is utilized to measure the density of the muddy liquid.

In a measurement device of the above type, which is inserted directly into a muddy liquid to measure the density thereof, it is unnecessary to transfer the muddy liquid for the sampling thereof. Accordingly, the measurement device is free from the problem that the pipes become clogged up with mud, and it does not need a large installation space. Furthermore, the measurement device is small in size and light in weight, and therefore it can be readily handled. In addition, the measurement device is automatically cleaned by a seal member which is provided at the end of a piston adapted to introduce the muddy liquid into the container, which contributes to improvement of the measurement accuracy and the reliability. Moreover, as the reliability of its consumable components (such as for instance the light emitting unit) is improved, it is unnecessary to replace these components for at least one year.

Although the conventional density meter is advantageous as described above, it still involves a problem of calibration. With the conventional density meter, before it is set in a muddy liquid to be measured, calibration is carried out by putting a transparent liquid (pure water), a standard specimen (formazine or kaolin) or a liquid having a known density in a transparent inner cylinder of the meter. After the calibration has been achieved, the densitometer is set in the muddy liquid to start the measurement of the density of the muddy liquid.

However, after the density meter has been used for a long period, it is impossible for the density meter to accurately measure the density of a liquid with the value which has been set initially, because of vibrations in characteristics of the components, deterioration of the components, and variations of the environmental conditions. Therefore, it is necessary to take the density meter out of the muddy liquid to recalibrate it at suitable time intervals (at least once a month). The density meter thus recalibrated is set in the muddy liquid again. However, such calibration takes much more time and labor than the replacement of the components (such as for instance the light emitting unit). Thus, even if the reliability of the density meter has been improved, it cannot be said that it is free of maintenance.

SUMMARY OF THE INVENTION

Accordingly, an object of this invention is to provide a density meter in which all of the above-described difficulties accompanying a conventional density meter have been eliminated.

Another object of the invention is to provide a density meter whose calibration can be achieved with the density meter maintained in the muddy liquid to be measured.

A further object of the invention is to provide a density meter high in accuracy whose maintenance can be accomplished in a relatively short time.

The foregoing objects and other objects of the invention have been achieved by the provision of a density meter immersed in a liquid to be measured so as to optically measure the density thereof. The density meter comprises: a density measurement system in which the liquid is sucked into a transparent inner cylinder by moving a piston upwardly and the density of the liquid is measured by an optical system provided outside the transparent inner cylinder, and a calibration system in which a calibration liquid flow path is formed in such a manner that the outlet of the calibration liquid flow path is communicated with the transparent inner cylinder and is positioned above a position at which the end of the piston is set in density measurement. During calibration, the piston is raised to a position higher than the position of the calibrating liquid flow path outlet to introduce a calibrating liquid into the transparent inner cylinder to calibrate the density meter by the optical system.

BRIEF DESCRIPTION OF THE DRAWINGS

Various other objects, features and attendant advantages of the present invention will be more fully appreciated as the same becomes better understood by reference to the following detailed description when considered in connection with the accompanying drawings, wherein like reference characters designate like or corresponding parts throughout the several views, and wherein.

DETAILED DESCRIPTION OF THE PREFERRED EMBODIMENTS

Figure 1:
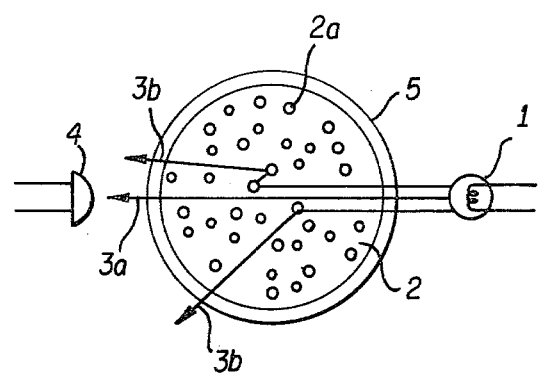
FIG. 1 is an explanatory diagram of the principle of an optical density measurement.

FIG. 1 is an explanatory diagram providing a description of the principle of optically measuring the density of a muddy liquid. A light emitting unit 1 is provided on one side of a container 5 in which a muddy liquid 2 to be measured has been put. The light emitting unit 1 applies light toward the muddy liquid 2. The light 3a passed through the muddy liquid and/or light scattered by suspended solids 2a in the muddy liquid is received by a light receiving unit 4, so that the density of the muddy liquid is determined from the output signal level of the light receiving unit 4.

Figure 2A:
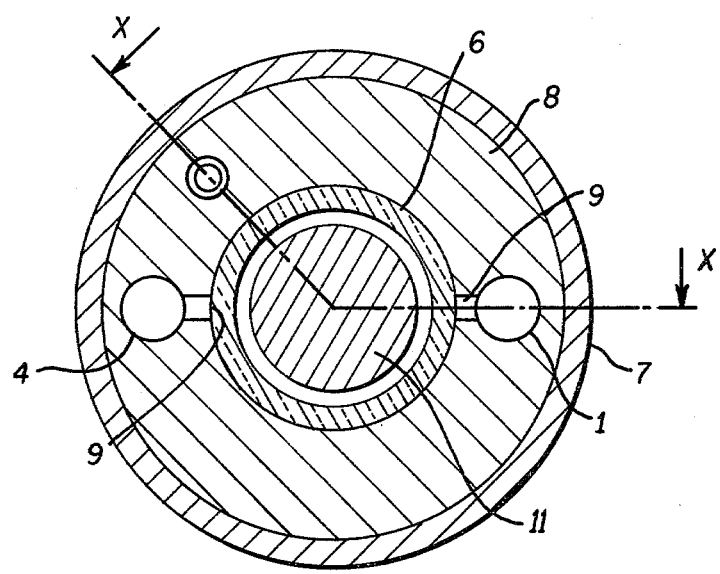
FIG. 2(A) is a cross-sectional view showing one example of a density meter according to this invention.

One example of a density meter utilizing an optical means according to this principle is that shown in FIG. 2. The density meter comprises a transparent inner cylinder 6 in which a muddy liquid is placed, an outer cylinder 7 provided outside the inner cylinder 6 and spaced a predetermined distance from the inner cylinder 6, and a cylindrical holder 8 inserted between the inner cylinder 6 and the outer cylinder 7, the cylindrical holder 8 incorporating a light emitting unit 1 and a light receiving unit 4 which are mutually opposed through the inner cylinder 6. The density meter further comprises light paths 9 which are provided on a line according to the light emitting unit 1 and the light receiving unit 4 in the holder 8. A piston 11 having a seal member 10 at the end is inserted into the inner cylinder 6, so that as the piston 11 is moved up and down, the muddy liquid is sucked into or discharged out of the transparent inner cylinder 6.

One or more flow paths 22 are formed in the holder 8 incorporating the light emitting unit 1 and the light receiving unit 4 in such a manner that each flow path 22 is communicated with a calibrating liquid pipe 21 which is inserted into the holder 8. The flow paths 22 are extended through the wall of the transparent inner cylinder 6, and are opened as flow path outlets 22a in the wall. It is preferable that each flow path outlet 22a is above the light paths 9.

Figure 2B:
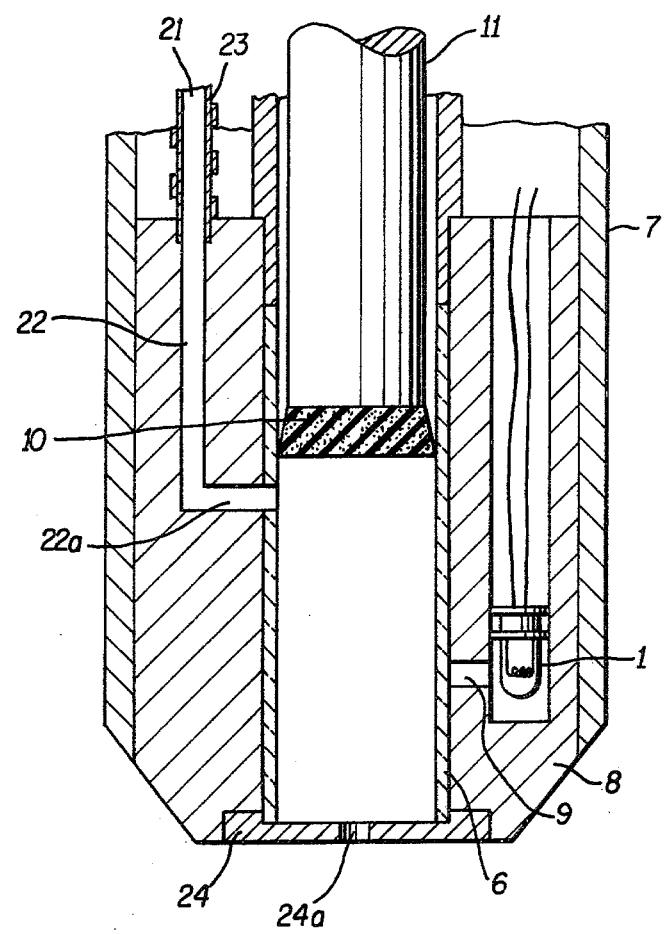
FIG. 2(B) is a sectional view taken along line X—X of FIG. 2(A)

An anti-freezing heater 23 is wound on the calibrating liquid pipe 21 so as to prevent the freezing of the calibrating liquid. A transparent inner cylinder receiving plate 24 is provided at the end of the transparent inner cylinder 6. A hole 24a much smaller in diameter than the inside diameter of the transparent inner cylinder 6 is formed in the plate 24. FIG. 2(B) is a sectional view taken along line X—X in FIG. 2(A). Therefore, the light receiving unit 4 is not shown in FIG. 2(B).

Figure 3A:
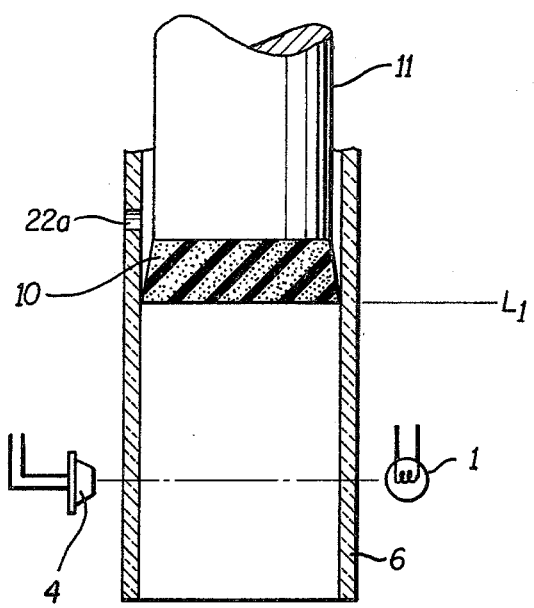
FIG. 3(A) is an explanatory diagram of the position which is taken by a piston in density measurement.
Figure 3B:
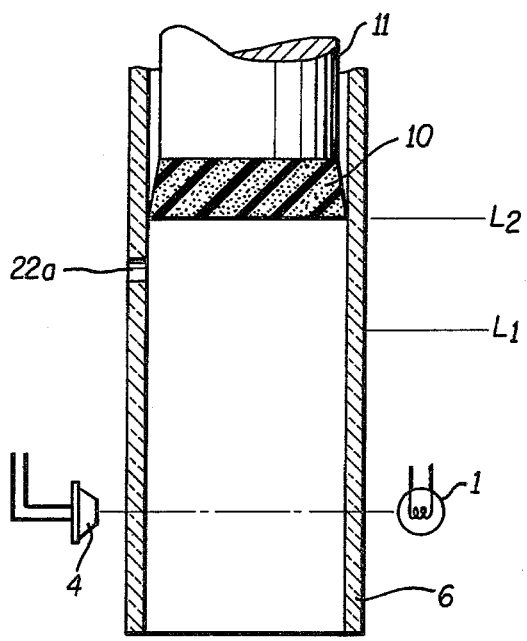
FIG. 3(B) is an explanatory diagram of the position which is taken by the piston in the calibration of the density meter.

The density of the muddy liquid 2 is measured as follows: First, the piston 11 is moved upwardly to suck the muddy liquid into the transparent inner cylinder 6 through the hole 24a. In this case, the piston 11 is stopped before the seal member 10 reaches the flow path outlet 22a of the calibrating liquid, i.e. at a position $L_1$ as shown in FIG. 3(A). Thereafter, the piston 11 is reciprocated with the position $L_1$ as the upper limit. Accordingly, as long as the piston is operated so that the seal member 10 is not moved above the upper limit, that is the position $L_1$, the calibrating liquid is never mixed into the muddy liquid, and therefore the density of the muddy liquid can be measured according to the conventional method.

Accordingly, when using the density meter, after the muddy liquid has been sucked into the transparent inner cylinder 6 by lifting the piston 11, the muddy liquid 2 is irradiated by the light emitting unit 1. The light from the light emitting unit 1 is applied to the light receiving unit 4 through the light path 9, the wall on one side of the inner cylinder 6, the muddy liquid 2, the wall on the opposite side of the inner cylinder 6 and the light path 9, in the stated order. The light thus applied is converted into an electrical signal by the light receiving unit 4, which is outputted to external equipment. Since the level of the electrical signal thus outputted is decreased in proportion to the density of the muddy liquid, the density of the muddy liquid can be determined by detecting the level of the electrical signal.

Calibration of the density meter is carried out as follows:

First, the piston 11 is moved upwardly until the lower end of the seal member 11 at the end of the piston is set at a position $L_2$ which is above the calibrating liquid flow path outlet 22a, so that the flow path 22 is communicated with the transparent inner cylinder 6. Under this condition, the calibrating liquid is introduced into the calibrating liquid pipe 21 from outside. As a result, the calibrating liquid is allowed to flow into the transparent inner cylinder 6 through the calibrating liquid pipe 21, the flow path 22 in the holder 8 and the outlet 22a. The calibrating liquid is supplied under pressure into the transparent inner cylinder 6. Therefore, the muddy liquid 2 which has been provided in the transparent inner cylinder 6 is caused to flow through the hole 24a, as a result of which the inner cylinder 6 is filled with the calibrating liquid instead of the muddy liquid 2.

Now, the density meter can be calibrated by using the light emitting unit 1 and the light receiving unit 4 similarly as in the measurement of the density of the muddy liquid 2. More specifically, the calibration of the density meter is carried out by controlling a processing circuit (not shown) so that a light reception signal level becomes zero when the light receiving unit 4 receives light from the light emitting unit 1 through the calibrating liquid.

In winter, it is necessary to carry out the calibration after the anti-freezing heater 23 has been energized, to prevent the freezing of the calibrating liquid. Furthermore, in order to discharge the muddy liquid 2 more readily, the hole 24a of the transparent inner cylinder receiving plate may be tapered from the inside, or a plurality of calibrating liquid flow paths 22 may be provided. It goes without saying that it is not always necessary to provide or form the flow path 22 in the holder 8.

As is apparent from the above description, according to the invention, the calibrating liquid flow path communicating with the transparent inner cylinder is formed so that the calibrating liquid can be supplied into the transparent inner cylinder from outside, and accordingly the calibration of the density meter can be achieved with the density meter set for measurement. Therefore, the troublesome operation where the density meter is taken out of the muddy liquid for recalibration is eliminated according to the invention. Therefore, the calibration can be quickly and readily achieved. Furthermore, by varying the stroke of the piston, the density measurement system is switched over to the calibration system and vice versa. Therefore, even in the case where the density meter in the calibration system is set to perform the ordinary density measurement, the muddy liquid never flows into the calibration liquid flow path, and no mud can stick to the calibration liquid flow path.

If the supply of the calibrating liquid is started and stopped by using an electromagnetic valve or the like (not shown), then manual calibration can be substantially eliminated, which provides a great improvement for maintenance.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A density meter adapted to be immersed in a liquid whose degree of opacity is to be optically measured, comprising:
    a density measurement system including a hollow inner cylinder having an inlet, a piston movable in said cylinder and an optical system externally associated with said cylinder at a first distance from said inlet; and a calibration system comprising a calibration liquid flow path having an outlet communicating with said cylinder at a point on said cylinder having a second distance from said inlet greater than said first distance, whereby said calibration system is activated by raising said piston to a position further from said inlet than said second distance.

2. The meter of claim 1 including a plurality of said calibrating liquid flow paths.

3. The meter of claim 1 wherein said inlet is located on a plate covering one end of said cylinder, the diameter of said inlet being less than that of said cylinder.

4. The meter of claim 1 wherein said calibrating liquid flow path includes heater means.

5. A method for optically measuring the density of a liquid, comprising:

immersing a hollow inner cylinder having an inlet at one end into the liquid to be measured;

moving a piston in said cylinder away from said inlet to draw said liquid into said cylinder;

utilizing an optical system externally associated with said cylinder at a first distance from said inlet to measure the degree of opacity of said liquid; and calibrating said meter after a predetermined period of time by further moving said piston away from said inlet beyond the outlet of a calibration liquid flow path, whereby the calibration liquid in said calibration liquid flow path fills said cylinder.

* * * * *